United States Patent
Bauman et al.

(10) Patent No.: US 8,123,766 B2
(45) Date of Patent: Feb. 28, 2012

(54) CIRCULAR STAPLER BUTTRESS

(75) Inventors: Ann M. Bauman, Flagstaff, AZ (US);
Stuart E. Broyles, Flagstaff, AZ (US);
Jerald M. Crawley, Flagstaff, AZ (US);
John R. Daugherty, Flagstaff, AZ (US);
Norman Pih, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 978 days.

(21) Appl. No.: 12/015,087

(22) Filed: Jan. 16, 2008

(65) Prior Publication Data

US 2008/0161832 A1 Jul. 3, 2008

Related U.S. Application Data

(63) Continuation of application No. 10/944,149, filed on Sep. 16, 2004, now Pat. No. 7,547,312, which is a continuation-in-part of application No. 10/666,204, filed on Sep. 17, 2003, now abandoned.

(51) Int. Cl.
*A61B 17/08* (2006.01)
*A61B 17/04* (2006.01)

(52) U.S. Cl. ............... 606/151; 606/153; 227/180.1

(58) Field of Classification Search ......... 606/75–77, 606/153, 214, 215, 219, 220; 227/175.2, 227/179.1, 180.1, 213, 220; 411/161, 531, 411/542, 544, 546
See application file for complete search history.

(56) References Cited

U.S. PATENT DOCUMENTS

| | | | |
|---|---|---|---|
| 2,191,101 A | * | 2/1940 | Stellin ........................... 411/161 |
| 3,953,566 A | | 4/1976 | Gore |
| 4,592,354 A | | 6/1986 | Rothfuss |
| 4,665,917 A | | 5/1987 | Clanton et al. |
| 5,104,025 A | | 4/1992 | Main et al. |
| 5,222,963 A | | 6/1993 | Brinkerhoff et al. |
| 5,250,058 A | | 10/1993 | Miller et al. |
| 5,263,629 A | | 11/1993 | Trumbull et al. |

(Continued)

FOREIGN PATENT DOCUMENTS

DE 19924311 5/1999
(Continued)

OTHER PUBLICATIONS

Supplementary European Search Report, EP04 78 4459, May 26, 2010, Munich, 2 pages.

*Primary Examiner* — Julian Woo
(74) *Attorney, Agent, or Firm* — Andrea W. Burke

(57) ABSTRACT

A buttress for use with circular surgical staplers that does not require adhesive to securely fasten the buttress to the stapler. Following cutting and stapling by the circular stapler, the buttress has an adaptive opening through its central region with a diameter smaller than the outer diameter of the stapler anvil. Because of relief features built into the buttress, the stapler anvil may be pulled through the buttress material without causing permanent alteration to the buttress. These relief features may be provided regardless of whether the buttress is made of inelastic or elastic materials. The buttress is generally circular in shape with an outer diameter sized to coincide with the outer diameter of the stapler body staple compression surface and the outer diameter of the anvil compression surface of a circular stapler with which it is used. Prior to surgical use, the buttress is attached to the stapler with disruptable portions extending from outer perimetal areas of the buttress.

24 Claims, 18 Drawing Sheets

U.S. PATENT DOCUMENTS

| | | | |
|---|---|---|---|
| 5,346,501 | A | 9/1994 | Regula et al. |
| 5,468,253 | A | 11/1995 | Bezwada et al. |
| 5,503,638 | A | 4/1996 | Cooper et al. |
| 5,713,920 | A | 2/1998 | Bezwada et al. |
| 5,752,965 | A | 5/1998 | Francis et al. |
| 5,908,427 | A | 6/1999 | McKean et al. |
| 5,964,774 | A | 10/1999 | McKean et al. |
| 6,063,097 | A | 5/2000 | Oi et al. |
| 6,099,551 | A | 8/2000 | Gabbay |
| 6,165,217 | A | 12/2000 | Hayes |
| 6,309,423 | B2 | 10/2001 | Hayes |
| 6,325,810 | B1 | 12/2001 | Hamilton et al. |
| 6,468,313 | B1 | 10/2002 | Claeson et al. |
| 6,503,257 | B2 | 1/2003 | Grant et al. |
| 6,503,259 | B2 | 1/2003 | Huxel et al. |
| 6,592,597 | B2 | 7/2003 | Grant et al. |
| 6,638,285 | B2 | 10/2003 | Gabbay |
| 6,656,193 | B2 | 12/2003 | Grant et al. |
| 7,128,748 | B2 * | 10/2006 | Mooradian et al. ........ 227/180.1 |
| 2003/0178465 | A1 | 9/2003 | Bilotti et al. |
| 2003/0183671 | A1 | 10/2003 | Mooradian et al. |
| 2005/0245965 | A1 | 11/2005 | Orban, III et al. |

FOREIGN PATENT DOCUMENTS

| | | |
|---|---|---|
| JP | 2000-166933 | 6/2000 |
| WO | 01/54594 | 2/2001 |
| WO | 03/082126 | 9/2003 |
| WO | 03/105698 | 12/2003 |

* cited by examiner

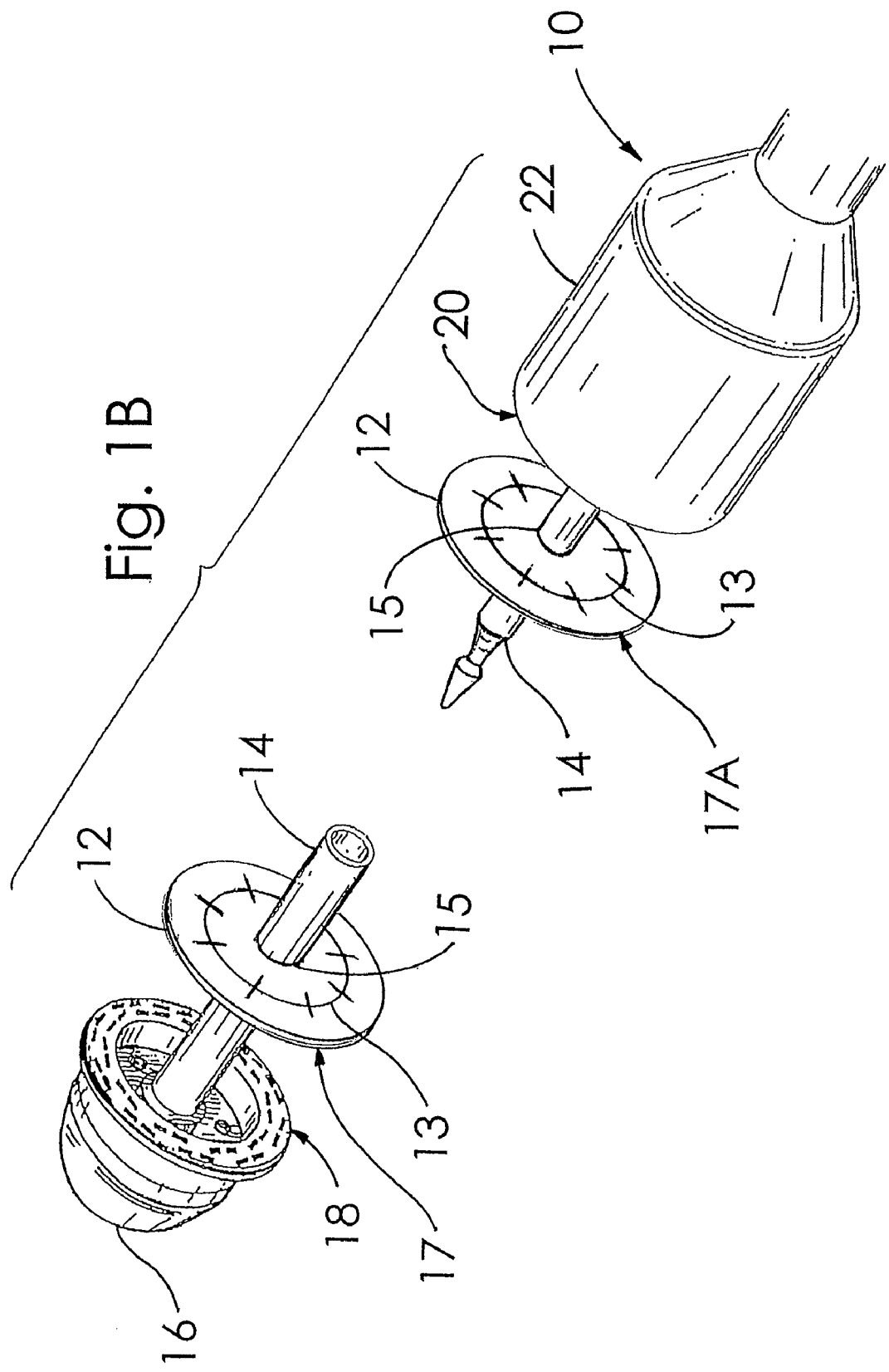

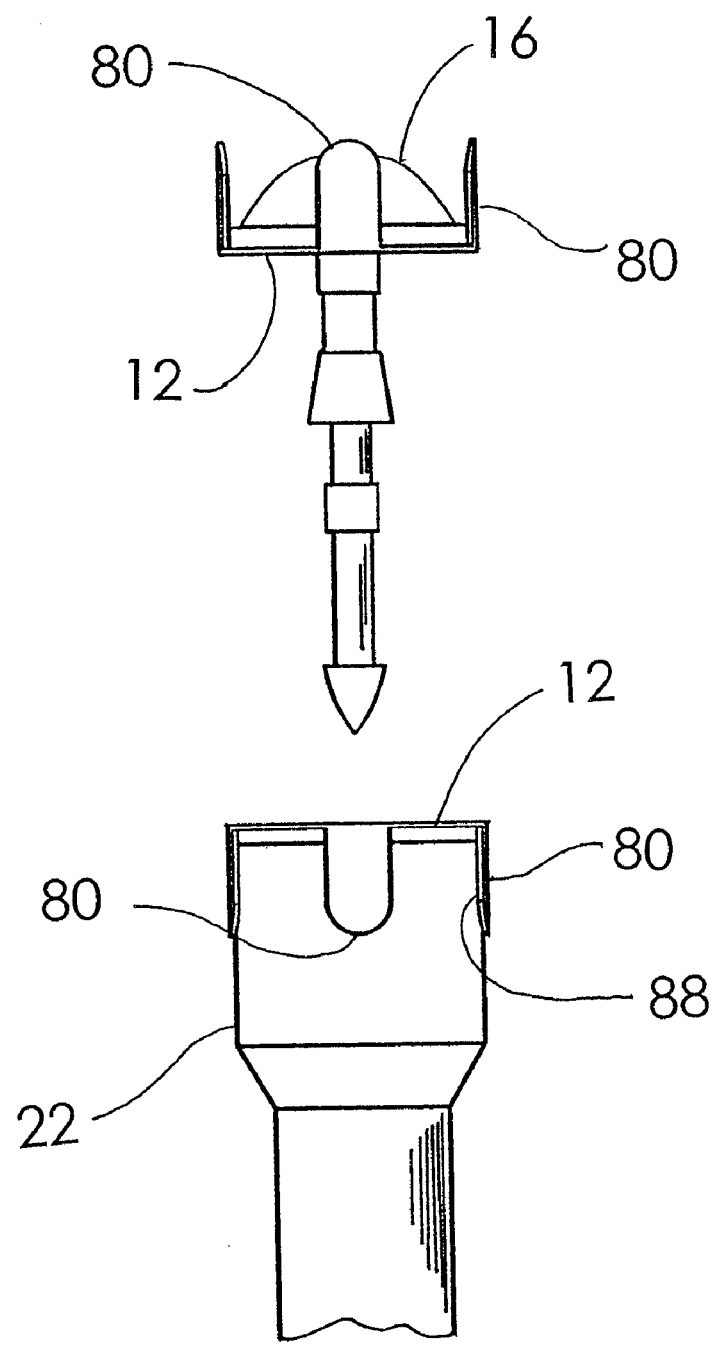

CIRCULAR STAPLER BUTTRESS

CROSS REFERENCE TO RELATED APPLICATIONS

This application is a continuation of U.S. application Ser. No. 10/944,149, filed Sep. 16, 2004, now U.S. Pat. No. 7,547,312, which is a continuation-in-part of U.S. application Ser. No. 10/666,204, filed Sep. 17, 2003, now abandoned, which is incorporated herein by reference.

FIELD OF THE INVENTION

The present invention relates to the field of surgical buttresses.

BACKGROUND OF THE INVENTION

A circular stapler is one device that can be used in surgical applications for the joining of body tissue. In the area of surgical anastomotic stapling, it can be used for joining pieces of tissue in a manner such that a continuous pathway, lumen, or surgical opening, is formed after the tissue is stapled together. This lumen is formed when a circle of staples is used to join two pieces of tissue after which the tissue interior to the innermost circle of staples is cut out by a concentric circular retractable blade. Retraction of the circular stapler removes the cut tissue to form a lumen. An example of a circular stapler is given in U.S. Pat. No. 5,104,025 to Main et al. Other devices and methods can also be used to produce anastomoses.

When used in surgery for colorectal disorders the circular stapler is used to reform the colon into a continuous lumen after a section is removed for treatment of the disease state. Concerns about leakage of the colon contents into the peritoneal cavity from the anastomosis site are prevalent during this type of surgery. A complete seal between the pieces of tissue that are joined is desirable to prevent leakage. Another concern in colon resections is reduction of the lumen diameter after surgery. This reduction in diameter would result in the restriction of the passage of biological material.

Using a stapler that forms a lumen with a diameter close to that of the preoperative healthy colon is desirable to prevent these flow restrictions. Typically the circle of staples formed is between 2-4 cm in diameter and is made from 20 to 40 small, metallic staples. Due in part to the presence of these metallic staples, another concern in tissue resection is tearing of the tissue at the anastomosis site.

Modifications to circular staplers as well as the development of other devices have been described to address the concerns that may occur during stapling of body tissue and the formation of a tissue anastomosis. A device used to create an anastomosis without staples is described in U.S. Pat. No. 5,222,963 to Brinkerhoff et al. and U.S. Pat. No. 5,250,058 to Miller et al. This device uses a tissue coupler made from a bioabsorbable polymer. A concern in using this device is the risk of tissue separation at the anastomosis site after the polymer has been absorbed by the body. A similar concern is shared for the device described in U.S. Pat. No. 5,346,501 to Regula et al., as it also uses only a bioabsorbable material for the formation of the anastomosis.

To alleviate the concern about tissue separation after the absorption of a bioabsorbable material, non-absorbable biocompatible metal staples can be used to form the anastomosis. However, leakage and/or tearing at the site where the tissue is joined are concerns when only metal staples are used. In order to prevent leakage and/or tearing, supporting buttresses constructed of both non-bioabsorbable and bioabsorbable materials for use with surgical staplers have been described in various publications. U.S. Pat. No. 6,503,257 to Grant et al. teaches a method for using an adhesive to releasably attach a buttress construct to a surgical stapling instrument. This buttress addresses both the leakage and/or tearing concerns that occur during tissue stapling. The use of metal staples provides for the long-term joining of the tissue. However, the buttress must be carefully aligned onto the stapling instrument and a suitable adhesive must be used on the surfaces of both the buttress and the stapling instrument to secure the buttress to the stapling instrument. Further, withdrawing the anvil part of the stapler through the buttress may be difficult, as the inner diameter of the buttress is smaller than the outer diameter of the stapler anvil.

A potential concern about use of an adhesive substance applied to the buttress is incompatibility of the adhesive with the tissue in the patient that it contacts. One mode of this tissue contact may be between the adhesive-containing surface of the buttress and tissue of the patient in the area of the anastomotic junction. The adhesive may also be transferred onto the staple surfaces as they penetrate through the adhesive present on the buttress and may then be carried into the tissue of the patient. An alternative to using adhesive on the buttress would be to design the buttress with protrusions that extend from the perimeter of the buttress and which may be provided with adhesive. These protrusions could be used to securely fasten the buttress to the circular stapler body and to the circular stapler anvil. Further, these protrusions could be disruptably attached, connected or fastened to the buttress to allow the protrusions to separate from the buttress in a controlled fashion.

SUMMARY OF THE INVENTION

The present invention is in the form of a buttress reinforcement device for use with circular surgical staplers that does not require an adhesive substance between the buttress and stapler to securely fasten the buttress to the stapler. The present invention is designed with protrusions that extend from the perimeter of the buttress and which may be provided with adhesive. These protrusions are used to align and securely fasten the buttress to the circular stapler body and/or to the circular stapler anvil. Further, these protrusions are disruptably attached, connected, or fastened to the buttress allowing for separation of the protrusions from the buttress in a controlled fashion.

In a preferred embodiment, when used with a circular surgical stapler, a hole is cut in the central region of the buttress by the stapler's circular cutting blade. The diameter of the hole formed in the buttress by the stapler's circular cutting blade is smaller than the outer diameter of the stapler's anvil. Relief features built into the buttress allow the stapler anvil to pull through the hole created in the buttress by the stapler's circular cutting blade without causing substantial permanent alteration to the buttress. These relief features can be provided regardless of whether the buttress is made of inelastic or elastic materials.

The buttress can be generally circular in shape with an outer diameter sized to coincide with the outer diameter of the stapler body staple compression surface and the outer diameter of the anvil compression surface of a circular stapler with which it is used. Alternatively, the buttress material may be formed into other non-circular geometric shapes (e.g. octagons). Also, the buttress material can be sized to be larger than or the same as the outer diameter of the stapler body staple compression surface and the outer diameter of the anvil compression surface of a circular stapler with which it is used in order to allow for self-alignment. This self-alignment insures that the buttress is aligned to coincide with and cover the pattern of staples ejected from the stapler. The buttress may have a generally circular opening in its central region that is sized to closely fit the central shaft of a circular stapler with which it is used. Alternatively, the buttress may have slits or other openings cut in its central region to allow for fitting the buttress onto the central shaft of a circular stapler while retaining the self-alignment feature. In a preferred embodiment, the central region of the buttress is that area which is cut away from the buttress by the action of the stapler cutting blade. In addition to the central opening, the buttress may have a slit or other opening reaching from the central opening to the outer diameter of the buttress. This feature would allow the buttress to be placed onto the central shaft of a circular stapler even when the stapler anvil was already attached to the stapler body through the central shaft.

In one embodiment, the buttress can have a retaining ring, disk, or similar device within or around its central region with a central opening. This retaining ring, disk, or similar device can be used to aid in the retention of the buttress onto the central shaft of the circular stapler without requiring the use of an adhesive substance between the central shaft of the stapler and the buttress construct. The retention of the buttress onto the circular stapler allows for movement, removal, or repositioning of the circular stapler during operation without loss or displacement of the buttress from the stapler.

In a preferred embodiment, the buttress is provided with removable or disruptably connected protrusions extending from the outer perimeter of the buttress body. These protrusions are designed to conform to the circular stapler body and/or the circular stapler anvil head so that when folded, one side of each protrusion contacts the body of the circular stapler and/or the circular stapler anvil head. Further, the protrusions are provided with an adhesive on the side of the protrusion that contacts the circular stapler body and/or circular stapler anvil head so that when the protrusion is conformed to contact the body of the circular stapler and/or circular stapler anvil head the buttress is securely attached with the adhesive. The protrusions are rendered removable from the buttress with a disruptable feature placed therebetween. Examples of disruptable features can include a series of holes, perforations, weakened sections or other means to allow for the controlled separation between the buttress and the protrusions. An alternate means of producing a weakened section is making that section thinner in cross section than other parts of the buttress or protrusion.

A preferred bioabsorbable buttress is fabricated from a copolymer of poly(glycolide:trimethylene carbonate). The copolymer's polyglycolide component is commonly abbreviated as PGA for poly(glycolic acid), the chemical byproduct to which it degrades after hydrolysis. The poly(trimethylene carbonate) component is commonly abbreviated as TMC, with the copolymer itself typically referred to as PGA:TMC and accompanied with relative percentage composition by weight. A preferred embodiment of the buttress is made from a bioabsobable ABA triblock copolymer of 67% PGA:33% TMC (w/w), formed into a non-woven web as taught by Hayes in U.S. Pat. Nos. 6,165,217 and 6,309,423. Other fabrications, processes, and polymers can alternatively be used to produce an elastic bioabsorbable buttress, such as using the polymers described by Bezwada in U.S. Pat. Nos. 5,468,253 and 5,713,920. While the primary constituent polymer can be alternatively blended with other polymers or active or inactive agents prior to fabrication, the resulting buttress can be imbibed, coated, or otherwise loaded with therapeutic or other either bioactive or bioinactive materials.

Accordingly, one embodiment of the present invention is a reinforcement device for use with a circular stapler that is adapted to create and seal a surgical opening in a patient comprising a buttress adapted for mounting on the circular stapler, the stapler having an anvil that is larger in diameter than the surgical opening that is created by the stapler, wherein following stapling with the stapler, the buttress reinforces the surgical opening created by the stapler in the patient, wherein the buttress includes at least one adaptive opening created by the circular stapler which corresponds to the surgical opening in the patient, said adaptive opening when circular having a diameter smaller than the diameter of the anvil, and wherein the adaptive opening in the buttress allows the anvil to be removed therethrough without causing permanent alteration to the buttress.

Another embodiment of the present invention is a reinforcement device for use with a circular stapler adapted to create a substantially circular hole in a patient, said circular stapler having a stapler anvil portion with a first compression surface and a stapler body portion with a second compression surface, said reinforcement device comprising a first buttress having a first contact surface adapted to attach to said stapler anvil without use of an adhesive on said first compression surface and said first contact surface, a second buttress having a second contact surface adapted to attach to said stapler body without use of an adhesive on said second compression surface and said second contact surface, and wherein the first and second buttresses reinforce said hole created by said stapler in said patient when staples are applied.

BRIEF DESCRIPTION OF THE DRAWINGS

FIGS. 1A and 1B are perspective views of the bioabsorbable circular stapler buttresses mounted on a typical circular stapler and showing how the anvil portion of the circular stapler can be separated from the body of the stapler.

FIG. 8A shows a front view of a circular stapler anvil head with a buttress in position to be attached with protrusions with removable coverings removed from the protusions.

FIG. 8B shows a front view of a circular stapler body with a buttress attached using protrusions.

DETAILED DESCRIPTION OF THE DRAWINGS

Figure 1A:
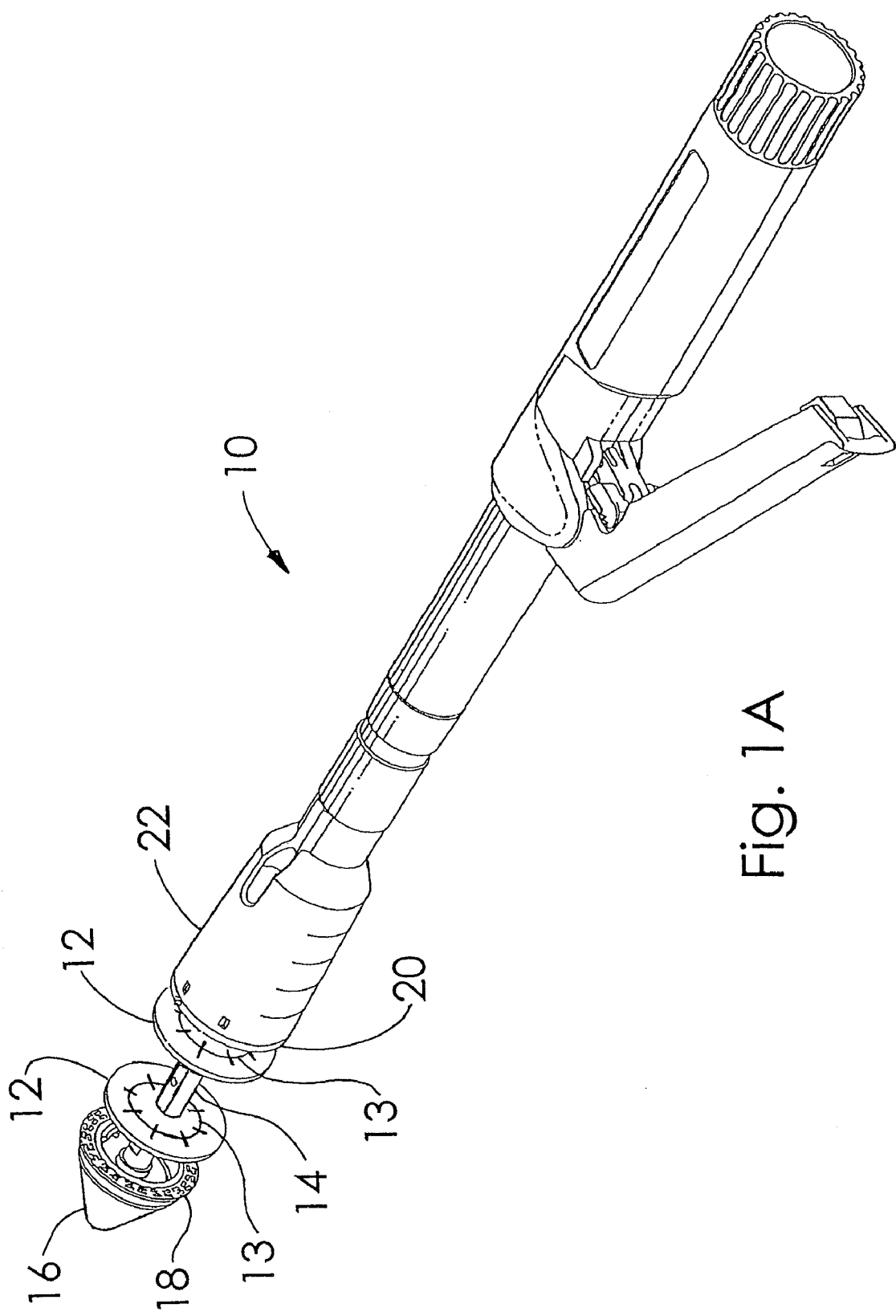

FIG. 1A is a perspective view of a typical circular surgical stapler 10 with two stapler buttresses 12 mounted on the central shaft 14 of the stapler. The stapler has an anvil head 16 with a staple compression surface 18. The anvil head 16 is removably attached to the stapler body 22 via the central shaft 14 as shown in FIG. 1B. The stapler body also has a compression surface 20 through which staples are ejected.

A first buttress 12 has a first surface 17 adapted to contact the anvil head staple compression surface 18. A second buttress 12 similarly has a second surface 17A adapted to contact the stapler body compression surface 20. Contact surfaces 17 and 17A are without adhesive. The central openings 15 in the buttresses 12 are sized to closely fit over the central shaft 14 so that the buttresses self-align onto the shaft. The central openings 15 in the buttresses 12 may be generally circular, slits or of any other geometric shape. Because of the size and shape of the central openings 15, the buttresses 12 are self-aligned and concentric to the cutting mechanism and stapler compression surfaces of the circular stapler. Each buttress 12 further has a member 13 that aids in attaching the buttresses 12 to the central shaft 14 of the stapler without the use of adhesive substance between the central shaft 14 of the stapler and the buttresses 12. The buttresses 12 can be placed onto the central shaft 14 of the circular stapler 10 when the stapler anvil 16 is separated from the stapler body 22 as shown in FIG. 1B. Alternatively, a buttress 12 with a slit or other opening reaching from the central opening to the outer diameter of the buttress can be placed onto the central shaft 14 of a circular stapler 10 when the stapler anvil 16 is connected to the stapler body 22 as shown in FIG. 1A.

Figure 2A:
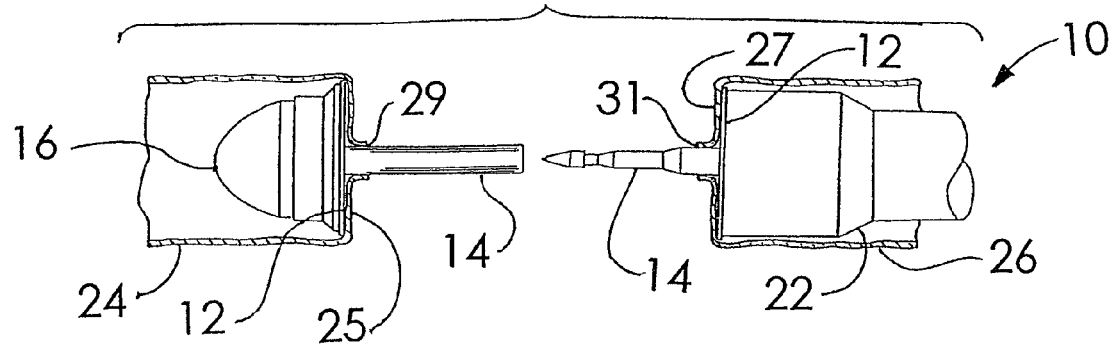
FIGS. 2A-2D are cross sectional views of colon undergoing resection using the buttresses of the present invention.

FIGS. 2A-2E show circular stapler buttresses 12 in use during, for example, a typical colon resection. FIG. 2A shows the stapler anvil head 16 and a buttress 12 placed inside the proximal end of a colon section 24, wherein proximal is defined as being closer to the heart of the patient being operated upon. An end of the central shaft 14 is protruding through a hole 29 formed in the colon tissue wall 25. The stapler body 22 and another buttress 12 are placed transanally inside a distal segment of the colon 26, wherein distal is defined as being farther from the heart of the patient being operated upon. Another end of the central tubular shaft 14 protrudes through a hole 31 formed in the distal colon tissue wall 27.

Figure 2B:
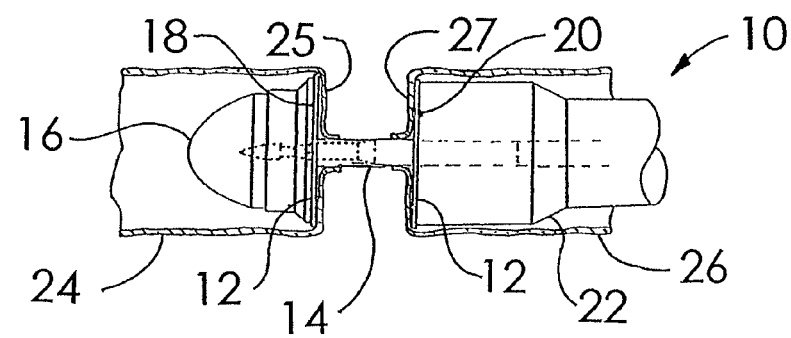

FIG. 2B shows the central shaft 14 with the anvil head 16 now joined to the stapler body 22. One buttress 12 is located between anvil compression surface 18 and the proximal colon tissue wall 25. Another buttress 12 is located between the body compression surface 20 and the distal colon tissue wall 27. The circular stapler 10 can be operated so as to pull the anvil head 16 towards the stapler body 22 so that the anvil head 16 and stapler body 22 are moved to within close opposition of each other.

Figure 2C:
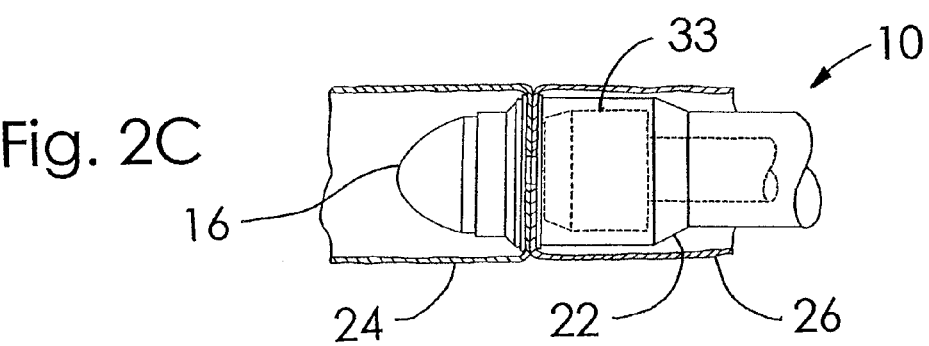

FIG. 2C shows the anvil head 16 and stapler body 22 in close proximity to each other in a position where the staples can be ejected through the compression surface on the stapler body 20 to pierce through the opposing tissue walls of both the proximal 25 and distal 27 colon wall sections and also though the buttresses 12 placed internally within each colon section. The staples upon ejection are bent as they impact on the compression surface 18 of the anvil head 16 and compression surface 20 of the stapler body 22, to form a shape designed to tightly hold the colon sections together. The staples pierce through the colon tissue walls 25, 27 and the buttresses 12 that are placed internally on each side of the joined colon sections. FIG. 2C also shows a generally circular concentric cutting blade 33 which can be actuated by the stapler operator when the stapler anvil head 16 has been moved to a position of close opposition to the stapler body 22. The generally circular concentric cutting blade 33 in the circular stapler body 22 moves upon actuation by an operator from a retracted position to an extended position to cut through the opposing walls of both the proximal 25 and distal 27 colon sections as well as the buttresses 12 placed internally in each colon section after the staples have been positioned and ejected. The generally circular concentric cutting blade cuts through the tissue adjacent to the inner diameter of the innermost row of staples to allow a continuous lumen to form between the now-joined colon sections. Therefore an anastomotic junction is created in the body tissue. After the anastomotic junction has been formed, the stapler is operated so that the stapler anvil head 16 is moved away from the staple body 22 to release the tissue compressed between the compression surfaces of the anvil head 18 and stapler body 20. The circular stapler 10 is withdrawn transanally carrying with it the sections of colon tissue and central regions of the buttresses 12, which were cut by the generally circular stapler blade.

Figure 2D:
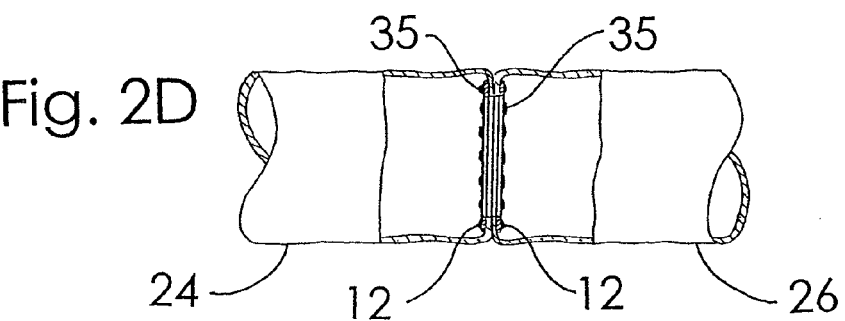
Figure 2E:
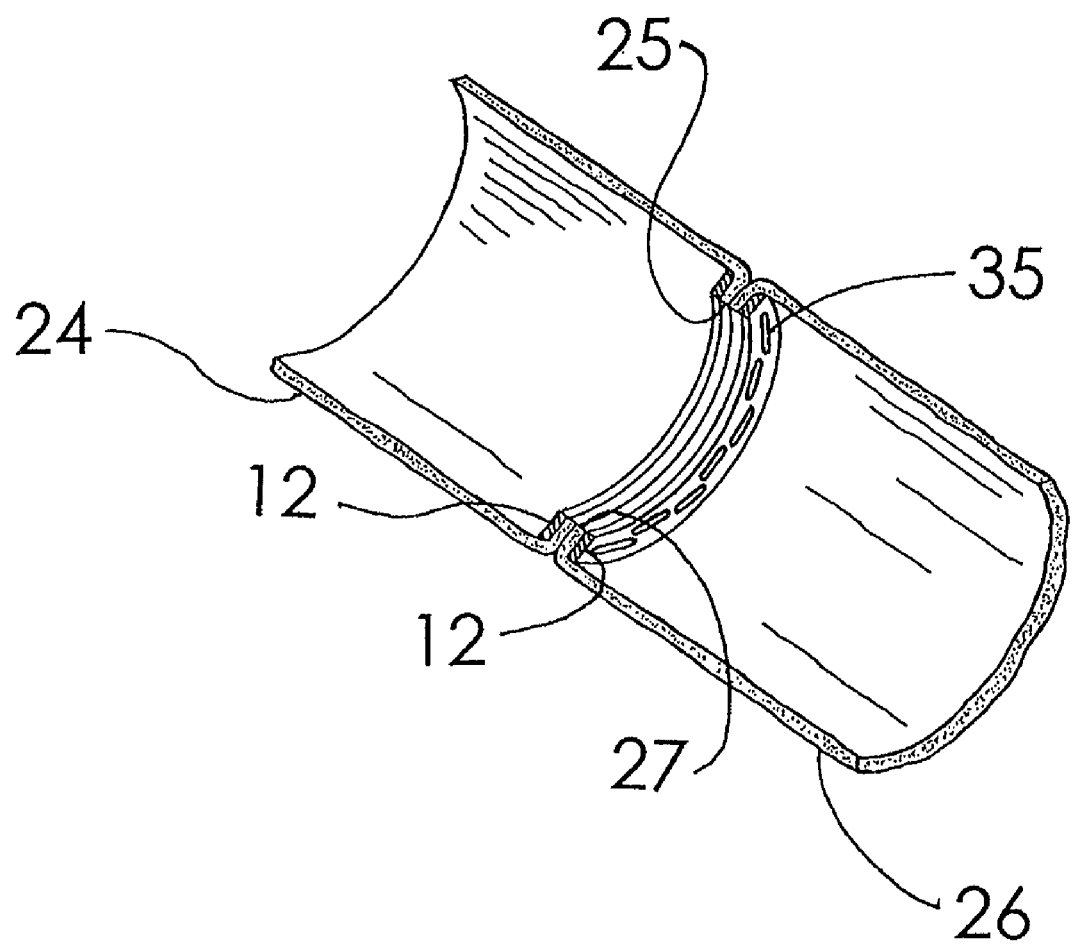
FIG. 2E is a perspective view of a longitudinal section of a colon undergoing resection using buttress of the present invention, that has been cut and stapled by a circular stapler.

FIGS. 2D and 2E show the proximal 24 and distal 26 colon sections now joined together. The staples 35, which are located circumferentially around the colon tissue, are held securely in place by means of the colon tissue walls, 25, 27 which have been reinforced with the buttresses 12. The buttresses 12 provide circumferential support to the anastomotic junction in addition to enhancing sealing between the staples and tissue. These buttresses 12 may therefore augment resistance to radial distension at the anastomotic junction.

The above description relates to use of the buttresses 12 of the present invention in forming a tissue anastomosis in a colon resection. It is anticipated that buttresses of this design could be used for other gastrointestinal applications, vascular applications and other applications in the human or animal body. Additionally, the above description describes the buttresses 12 both being placed internally within the colon segments. In an alternative use, a buttress 12 could be placed external to the colon segments. Further, buttresses 12 could be placed internally within each colon segment while another buttress could be placed externally between the colon segments. In another use, one buttress could be placed internally within one colon segment while another buttress could be placed externally between the colon segments. The number of buttresses 12 used and placement of the buttresses 12 in and around the relevant tissue sections is left to the surgeon.

The buttress 12 of the present invention may be fabricated from either bioabsorbable or non-absorbable biocompatible materials. These materials may be either hydrophilic or hydrophopic or rendered hydrophilic or hydrophobic by using an appropriate coating or imbibing process. For example, a normally hydrophobic material may be rendered hydrophilic using a coating of polyvinylalcohol crosslinked on the surface of the material. A preferred embodiment for the buttress of the present invention is a bioabsorbable ABA triblock copolymer of 67% PGA:33% TMC (w/w) formed into a self-cohering non-woven web as generally taught by Hayes in U.S. Pat. Nos. 6,165,217 and 6,309,423. Alternatively, this web or other buttress constructs may be fabricated from other biocompatible bioabsorbable polymers and copolymers composed from varying amounts of one or more of the following monomer examples: glycolide, d,l-lactide, l-lactide, d-lactide, p-dioxanone (1,4-dioxane-2-one), trimethylene carbonate (1,3-dioxane-2-one), $\epsilon$-caprolactone, gamma.-butyrolactone, delta.-valerolactone, 1,4-dioxepan-2-one, and 1,5-dioxepan-2-one. Other polymeric constituents of a bioabsorbable copolymer may include polyethylene glycol, polypropylene glycol, amino acids, anhydrides, orthoesters, phosphazines, amides, urethanes, and phosphoesters. Alternative copolymers may possess, in whole or in part, block, segmented, random, alternating, or statistical polymeric construction characteristics. Animal derived products such as elastin, collagen or decellularized submucosa, either absorbable (e.g. enzymatically degraded within the body) or rendered non-absorbable through chemical treatment (e.g., glutaraldehyde cross-linked bovine pericardium or porcine pericardium), may alternatively be utilized to provide a buttress construct. Various non-absorbable polymers may be utilized for buttress construction include but are not limited to polytetrafluoroethylene, fluorinated ethylene propylene (FEP), fluoroelastomers, polyurethanes, polyesters (e.g. polyethylene terephthalate), polyacrylamide, polyacetate, polypropylene, polydimethylsiloxane, and nylon. Of these, porous expanded polytetrafluoroethylene (ePTFE), generally made as taught by U.S. Pat. No. 3,953,566 to Gore, may provide a preferred non-absorbable buttress.

A preferred method of forming the buttress 12 using a bioabsorbable material is using a piece of 67%/33% PGA: TMC (w/w) that has been formed into a self-cohering non woven web into a thickness of approximately 0.25 mm following methods as generally taught by Hayes in U.S. Pat. Nos. 6,165,217 and 6,309,423. This piece of self-cohering non woven web is cut, for example, by a laser into a generally circular shape with an outer diameter made to coincide with the compression surface outer diameters for the anvil 18 and body 20 of a particular circular stapler. A variety of other cutting methods, such as die cutting, can be alternatively used. Due to the porous construction of the self-cohering non-woven web, various bioactive agents and carrier materials can be introduced into the porous interfiber interstices of the web or coated onto the fiber strands. Bioactive agents in this context refers to growth factors, chemotactic factors, morphogens, pharmaceuticals or drugs, catalysts, proteins, peptides or other biologically active molecules or genetically altered or native state living cells of autogenic, allogenic, xenogenic or recombinant origin that induce an intended biological response. Such substances include, but are not limited to antibiotics, organic or inorganic antimicrobials, healing factors, blood clotting agents, anticoagulants, antithrombotics, antispasmodics, immunosuppressives, antacids, acid inhibitors, and ulcer treating agents. Other fillers can include radiopaque substances to enhance visualization. Bioactive agents and fillers could be used with other porous and non-porous constructions for other bioabsorbable as well as non-absorbable materials.

FIGS. 3A-3E show top views of buttresses 12 with various relief features cut into them. These relief features form "adaptive openings" in the reinforcement material. These "adaptive openings" allow a larger diameter anvil 16 of a circular surgical stapler 10 to be pulled through the smaller diameter opening created by the cutting blade of the circular stapler without causing substantial permanent alteration to the reinforcement material. The relief features are preferably formed by laser cutting, although they could be made by a variety of other methods such as by use of a cutting die. The relief features are sized and placed so that some part of them remain on the portion of the buttress 12 that remains in the patient after the cutting action of the blade of a circular stapler. As will be further described, an adaptive opening may also be provided by making the perimeter of the adaptive opening corrugated, thereby providing extra material along the perimeter and accordingly increasing its flexibility in order to allow the stapler anvil to be withdrawn through the adaptive opening.

Figure 3A:
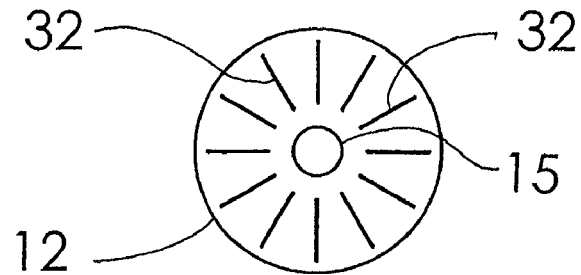
FIGS. 3A-3F show top views of various embodiments of the buttress.

FIG. 3A shows the top view of a buttress 12 with twelve equally spaced linear radial cuts 32 emanating from the area of a central opening 15.

Figure 3B:
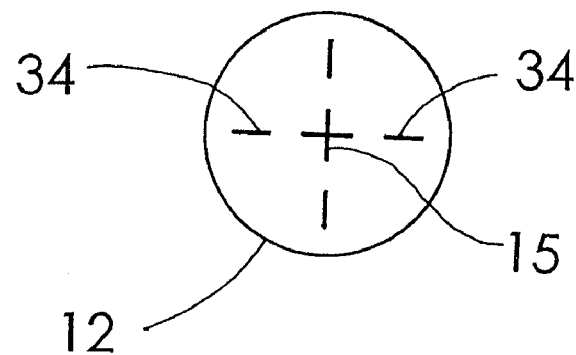

FIG. 3B shows the top view of a buttress 12 with four equally spaced linear cuts or slits 34 in a radial spoke type pattern emanating from the area of a central opening 15.

Figure 3C:
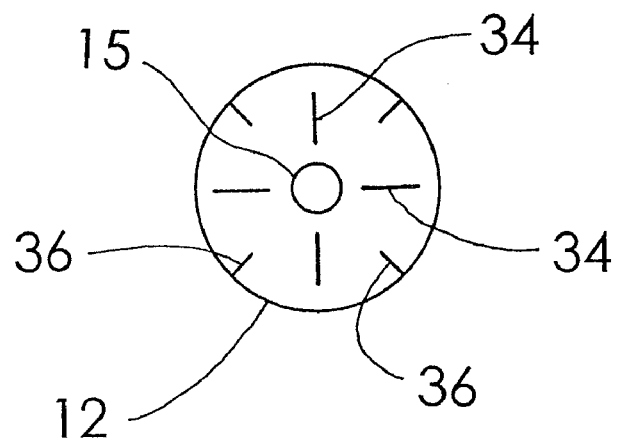

FIG. 3C shows the top view of a buttress 12 with four equally spaced linear cuts or slits 34 surrounding a central opening 15 as in FIG. 3B but with the addition of four radial cuts or slits 36 originating from the perimeter of the buttress 12.

Figure 3D:
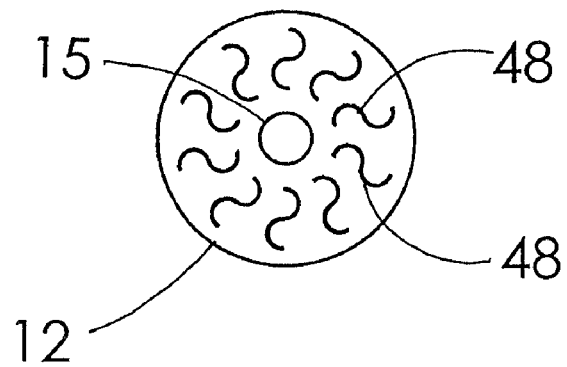

FIG. 3D demonstrates that the relief features can be other than straight lines. FIG. 3D shows the top view of a buttress 12 that has serpentine shaped relief features 48 emanating from the area of a central opening 15.

Figure 3E:
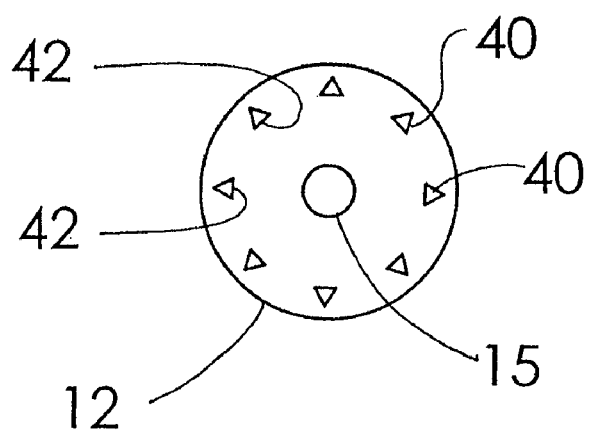

FIG. 3E demonstrates that other geometric figures could provide similar function to the operation of the buttress, showing the top view of a buttress 12 with a series of generally triangular shapes 40 that are arranged radially around a central opening 15. The bases of the triangular shapes 42 are placed to coincide with the outside diameter of the generally circular concentric cutting blade of the selected circular stapler.

Figure 3F:
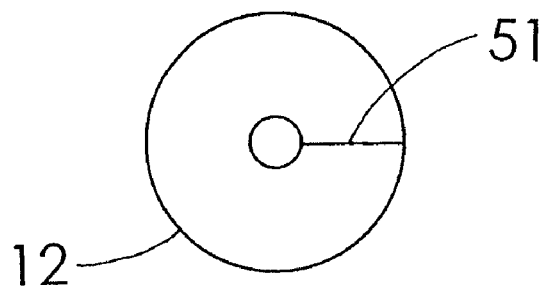

FIG. 3F shows a top view of a buttress 12 having a slit 51 through the entire width. It is apparent that, in addition to providing for an adaptive opening, the slit 51 allows the buttress 12 to be fitted over the central shaft 14 of the stapler without necessitating the prior removal of the anvil 16 from the stapler body 22.

Figure 3G:
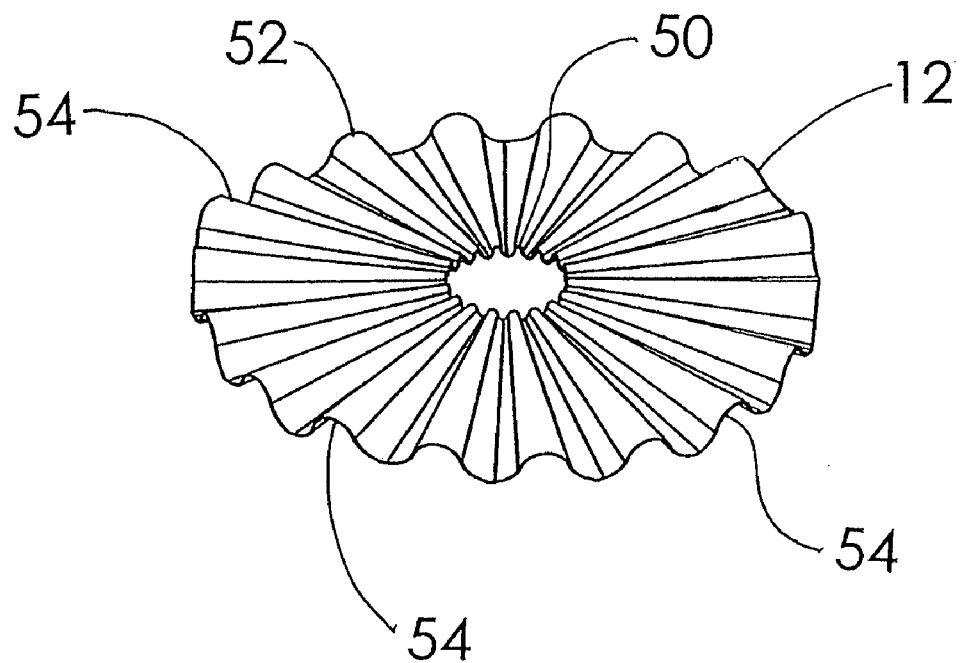
FIGS. 3G, 3H, 3J and 3K show perspective views of the buttress having various corrugations.

FIG. 3G is a perspective view of a buttress 12 showing an embodiment wherein the adaptive opening results from corrugations 54. FIG. 3G has an inner edge 50 and an outer edge 52 with corrugations 54 that are formed between the inner and outer edges 50, 52. These corrugations may be made, for example, by transversely cutting a short segment from a length of tubular material, and deforming the resulting ring-shaped segment by bending one edge inwardly to cause the inner hole whereby the extra material results in corrugations. Alternatively, a mold could be used to form the corrugations.

Figure 3H:
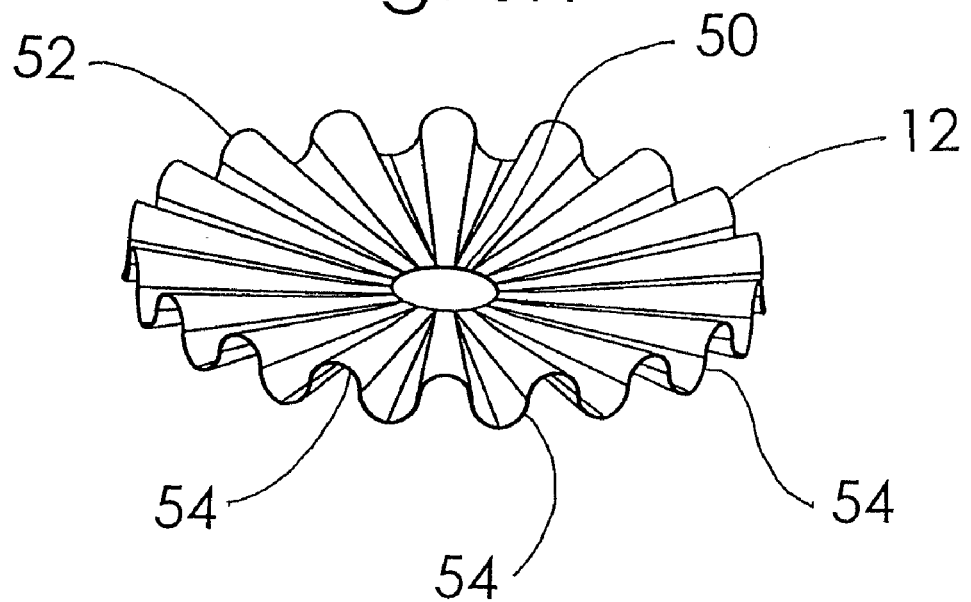

FIG. 3H is a perspective view of a buttress 12 showing an embodiment wherein the adaptive opening results from corrugations 54. FIG. 3H has an inner edge 50 and an outer edge 52 with corrugations 54 that are present at the outer edge 52 but not at the inner edge 50. In an alternate embodiment, the corrugations could be formed at the inner edge 50, but not at the outer edge 52.

Figure 3J:
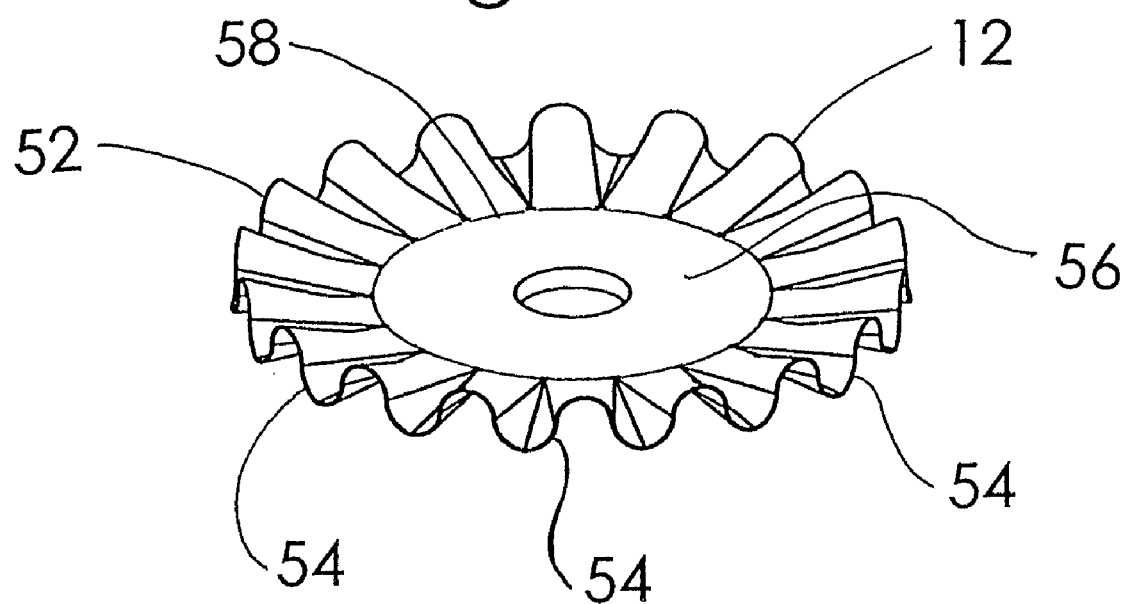

FIG. 3J is a perspective view of a buttress 12 showing an embodiment wherein the adaptive opening results from corrugations 54. FIG. 3J has a central non-corrugated or planar region 56 with a corrugated area from the outer perimeter of the corrugated or planar region 58 to the outer edge of the buttress 52.

Figure 3K:
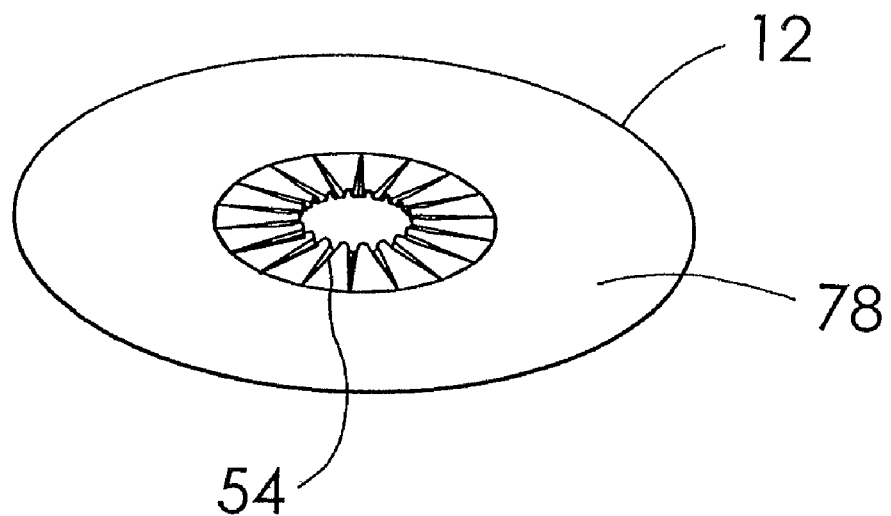

FIG. 3K is a perspective view of a buttress 12 showing an embodiment wherein the adaptive opening results from corrugations 54 of the inner region of the buttress. FIG. 3K has an outer non-corrugated or planar region 78 that surrounds the central region having corrugations 54.

In each of the buttresses depicted in FIGS. 3G, 3H, 3J, and 3K, the adaptive opening resulting from corrugations 54 are sized and placed so that some part of the adaptive opening remains on the portion of the buttress 12 that remains in the patient after the cutting action of the blade of a circular stapler.

It is anticipated that designs other than those depicted in FIGS. 3A-3H, 3J and 3K may be used for the relief features on the buttresses 12. These various relief features allow for the anvil head 16 of a circular stapler 10 to pass through a buttress 12 without tearing or substantially altering the buttress 12, even though the anvil head 16 compression surface 18 has an outer diameter larger than the inner diameter of the hole formed in the buttress 12 when a generally circular, concentric cutting blade of the circular stapler 10 has been used to cut the hole in the buttress 12.

Figure 6A:
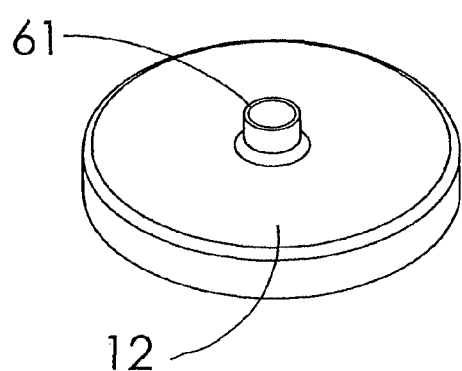
FIG. 6A shows a perspective view of a buttress allowing for self-alignment on the central shaft of a circular stapler.
Figure 6B:
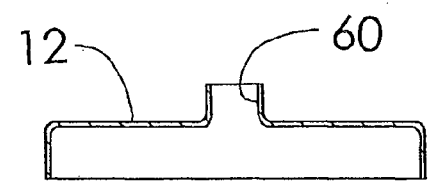
FIG. 6B shows a cross sectional view of a buttress allowing for self-alignment on the central shaft of a circular stapler.
Figure 6C:
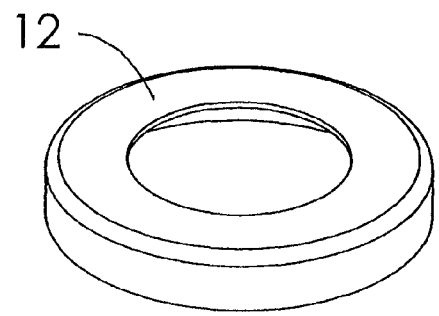
FIG. 6C shows a perspective view of a buttress allowing for self-alignment on the outer diameter of a stapler anvil head or stapler body compression surface.
Figure 6D:
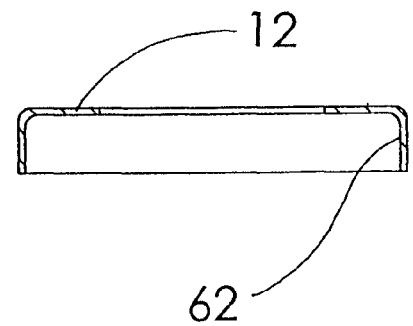
FIG. 6D shows a cross sectional view of a buttress allowing for self-alignment on the outer diameter of a stapler anvil head or stapler body compression surface.

Self alignment of the buttress 12 onto a circular surgical stapler is another important aspect of this invention. Self alignment insures that the buttress is generally aligned to coincide with and cover the pattern of staples ejected from the stapler. The buttress 12 may be self-aligned using an opening in its central region sized to closely fit the central shaft of a circular stapler with which it is used. Alternatively, the buttress 12 may be self-aligned using the outer diameter of the stapler anvil compression surface 18 and the outer diameter of the stapler body compression surface 20. FIGS. 3A-3H, 3J, 3K, 6A and 6B show buttresses 12 adapted to self align using openings in their central regions. FIG. 6A shows a perspective view of a buttress 12 which has an opening feature 61 in its central region. FIG. 6B shows a cross section of the buttress shown in FIG. 6A. Surface 60 in FIG. 6B contacts the outer diameter of the central shaft 14 (FIG. 1B) of a circular stapler 10. FIG. 6C shows a perspective view of a buttress 12 which is adapted to self align onto the outer diameter of the stapler anvil compression surface 18 (FIG. 1B) or outer diameter of the stapler body compression surface 20 (FIG. 1B). FIG. 6D shows a cross section of the buttress shown in FIG. 6C. Surface 62 in FIG. 6D contacts the outer diameter of the stapler anvil compression surface 18 (FIG. 1B) or outer diameter of the stapler body compression surface 20 (FIG. 1B) to insure self-alignment.

The buttress 12 can be made of a constant thickness or can be made of varying thickness, densities or materials of construction through their cross sections. Varying thicknesses, densities or materials of construction can be of advantage in some embodiments. For example, greater thickness or use of a denser material in the central region of the buttress would add rigidity, potentially aiding in self-aligning of the buttress 12 on the circular stapler 10. Thickness, density or material variations may also help to prevent deformation of the buttress 12 as the circular stapler is used in the process of pulling the stapler anvil 16 toward the stapler body 22 (as depicted in FIGS. 2B and 2C). This thicker or higher density material could be limited to the central region of the buttress so that the generally circular concentric cutting blade of the stapler 10 would cut through or around this thicker material and remove it while the stapler was being withdrawn. In another embodiment, thinner or less dense material could be made to generally coincide with the cutting diameter of the generally circular concentric cutting blade of the selected circular stapler to facilitate the cutting process. Alternatively, thicker, more dense or stronger material could be constructed into the buttress 12 so as to coincide with the areas where the staples are placed with thinner, less dense or weaker material used in other areas.

Figure 4A:
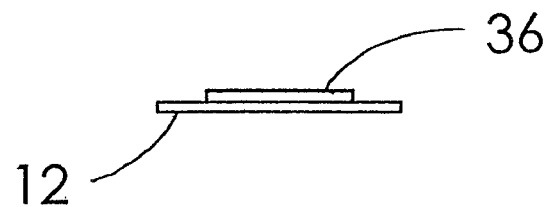
FIGS. 4A-4C show side views of three alternate embodiments of the buttress with varying thicknesses and densities.
Figure 4B:
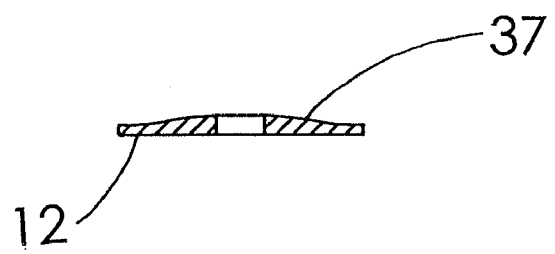
Figure 4C:
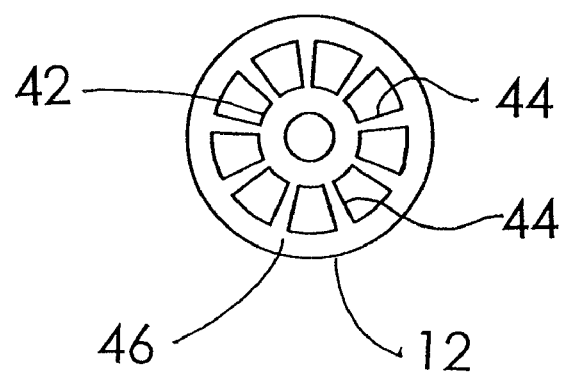

Three embodiments of buttresses 12 of varying cross sections are shown in FIGS. 4A-4C. FIG. 4A shows the side view of a buttress 12 that has a silicone disk 36 attached to it. The silicone disk 36 may be approximately 0.5 mm thick, made, for example, with Nusil MED 4080 (NuSil Technology, Carpinteria, Calif.) and can be provided with center hole sized to form a slight interference fit with the central shaft 14 of a circular stapler 10. The interference fit between the central shaft 14 of the stapler and the center hole in the silicone disk 36 provides for a means to securely fasten the buttress 12 to the circular stapler without an adhesive. The outer diameter of this silicone disk 36 is sized to correspond with the central region of the buttress 12, fitting within the diameter of the generally circular concentric cutting blade of a circular stapler 10.

One side of the silicone disc 36 is adhered to one side of the buttress 12 by covering one side of the disc 36 with a thin coating of a pressure sensitive adhesive formulation of silicone (e.g., NuSil MED 1356, NuSil Technology, Carpinteria, Calif.). After a 30 minute drying period, disc 36 may be placed onto one surface of buttress 12 with the adhesive coated surface of the silicone disk 36 facing towards the surface of the buttress 12 as illustrated in FIG. 4A. Compressive force is then applied to the silicone disk 36 to assure adequate bonding between of the silicone disk 36 to the buttress 12.

Other means of making the central section of the buttress 12 thicker may be used, such as using materials other than silicone or building up more self-cohering non-woven web thickness.

FIG. 4B shows the side view of a buttress 12 where the central region 37 is thicker due to the process of adding more material to the central region in comparison to the thickness adjacent the perimeter. FIG. 4C shows the top view of a buttress 12 where the central section 42 is made with thicker or higher density material. Spokes 44 emanating from the central section 42 are also made with thicker or higher density material. A perimeter area 46 of the buttress 12 as depicted can also be made with a thicker or higher density material to increase the strength of the material for staple reinforcement. The buttresses 12 depicted in FIGS. 3A-3E and 4A-4C and other designs that can be contemplated may also be constructed in a modular fashion such that individual materials can be combined to form the final device.

Additionally, buttresses 12 of various designs including those depicted in FIGS. 3A-3H, 3J, 3K, and 4A-4C can be used with a circular stapler that has a round or non-round central shaft. Circular staplers with non-round shafts with buttresses 12 having central openings corresponding to the shape of the shaft could facilitate indexing of the buttresses 12 to locations relative to the stapler anvil and body compression surfaces 18 and 20.

FIGS. 7A, 7B, 7C, 8A and 8B depict a preferred embodiment used to self-align and securely attach buttresses 12 to a circular stapler body 22 and/or to a circular stapler anvil 16.

Figure 7A:
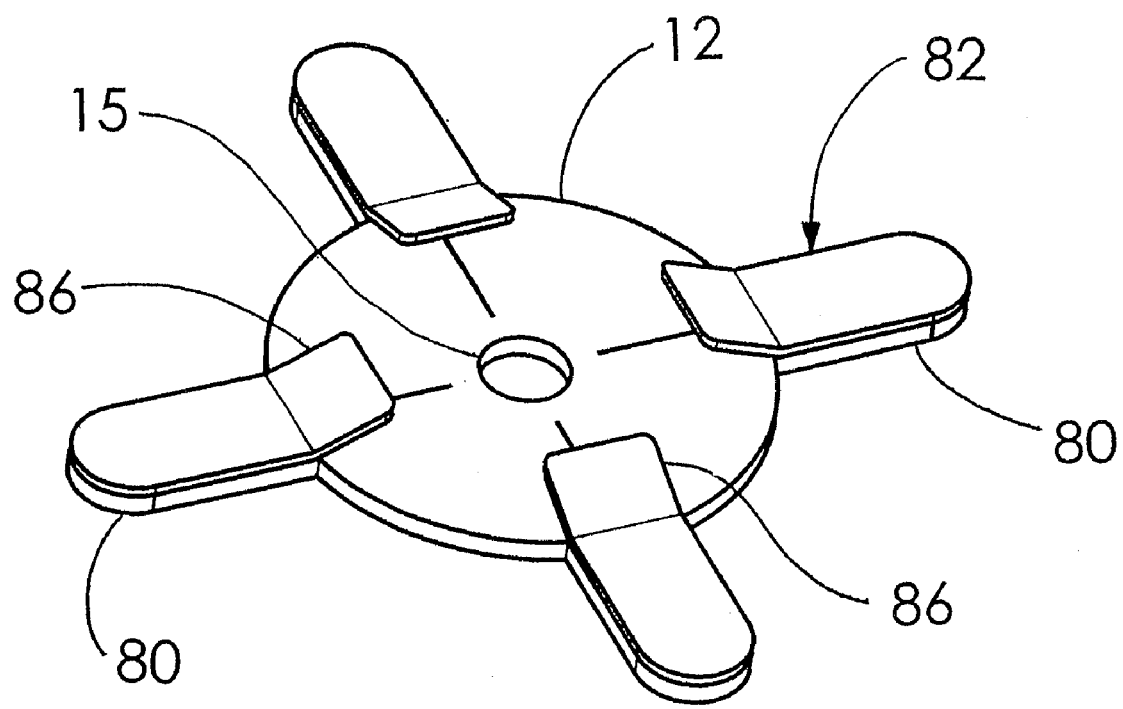
FIG. 7A shows a perspective view of a buttress with removable protrusions extending from the perimeter of the buttress.
Figure 7B:
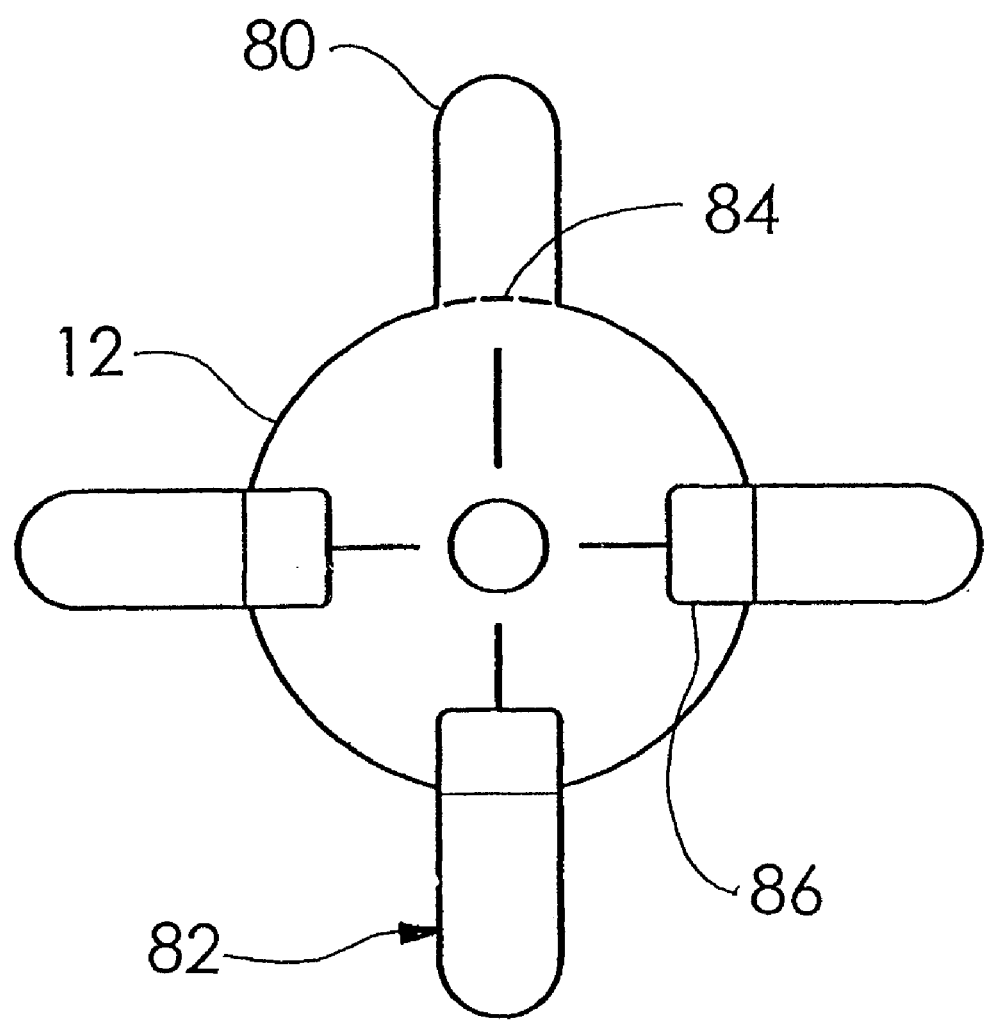
FIG. 7B shows a top view of a buttress with removable protrusions extending from the perimeter of the buttress with one removable covering removed.
Figure 7C:
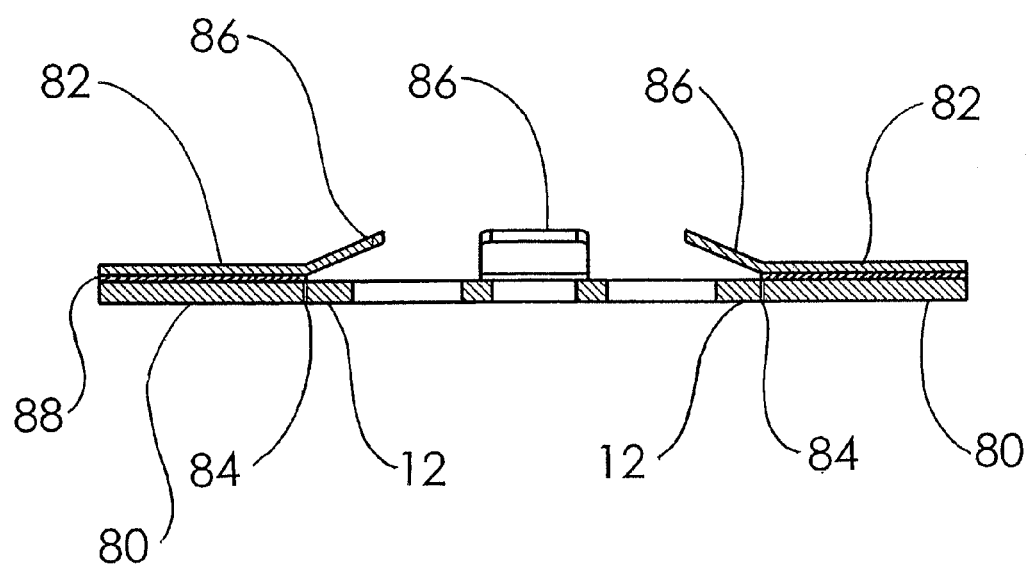
FIG. 7C shows a cross-sectional view of a buttress with removable protrusions extending from the perimeter of the buttress.

FIG. 7A shows a perspective view of a buttress 12 with four removable protrusions 80 extending from the perimeter of the buttress. The removable protrusions 80 are coated on one side with an adhesive substance that covers only the surfaces of the protrusions and not the buttress. The adhesive substance coated on one side of the protrusions 80 is covered by removable coverings 82 that protect the adhesive substance from inadvertent contact. Removable coverings 82 are shown in FIG. 7A as being only adhered to the sides of the protrusions 80 which are coated with adhesive, but not to the buttress 12, which has no adhesive on it. The portions of the removable coverings that overlap the buttress 12 are not adhered to the buttress 12 allowing for tab sections 86 that are easily grasped when removal of the coverings 82 is desired. FIG. 7B shows a top view of a buttress 12 with four protrusions 80 extending from the perimeter of the buttress with one removable covering 82 having been removed revealing disruptable sections 84 between the protrusion 80 and the perimeter of buttress 12. The disruptable sections 84 between the perimeter of buttress 12 and the protrusions 80 may be disrupted after the buttress 12 is attached to the anastomotic junction formed when staples are fired through the buttress 12 and tissue of the patient by the circular stapler and then the circular stapler is subsequently withdrawn from the patient allowing the protrusions 80 to detach from the buttress 12. The protrusions 80 after disruption at disruptable sections 84 stay attached to the circular stapler body 22 and/or circular stapler anvil head 16 while the buttress 12 remains in the tissue of the patient at the anastomotic junction that is formed. Alternatively, the disruptably attached protrusions, 80 may be detached from the buttress 12 at any other time by the operator if desired. FIG. 7C shows a cross-sectional view of a buttress 12 with protrusions 80 connected with disruptable sections 84 to the perimeter of the buttress. The protrusions 80 have an adhesive 88 between the protrusion 80 and the removable covering 82. A tab section 86 of each removable covering overlaps the buttress 12 but is not attached to either the buttress or to the protrusion 80. This unattached tab section 86 of the removable covering 82 can be used to grasp the removable covering 82 to facilitate its removal by the user.

FIG. 8A shows a front view of a circular stapler anvil head 16 with a buttress 12 in position to be attached to the circular stapler anvil head using protrusions 80 from which removable coverings 82 have been removed. The protrusions 80 are covered with an adhesive substance on only the side of the protrusions which will contact the anvil head when the protrusion is positioned to conform to the contours of the anvil head. FIG. 8B shows a buttress 12 attached to a circular stapler body 22 with protrusions 80 from which removable coverings 82 have been removed. These protrusions 80 are coated on one side only with an adhesive substance 88. The adhesive substance 88 contacts the circular stapler body 22 when the protrusions 80 are positioned to conform to the contours of the outer surface of the circular stapler body 22. Although four protrusions are shown attached to buttresses 12 in FIGS. 7A, 7B, and 7C, other numbers of protrusions may also be used. Additionally, the protrusions may be made in other lengths, widths or geometric shapes than those depicted. Also, the protrusions may be provided without adhesive should it be desired to secure the buttresses 12 to the circular stapler through other means, such as, for example with a suture, adhesive tape, or adhesives applied to the protrusions at the time of use. Alternatively, the removable coverings 82 may be left on the protrusions 80 should it be desired to not use the adhesive substance 88 to adhere the protrusions to the stapler body surfaces. Further, the protrusions 80 may be removed from the buttress 12 at any time by the operator should the operator deem the removal of the protrusions 80 from the buttress 12 to be more favorable to the procedure which is contemplated by the operator.

A buttress 12 can be constructed to exhibit either essentially elastic or essentially inelastic behavior. Essentially elastic behavior occurs when a buttress 12 is adequately deformable so as to allow an anvil head 16 of larger outer diameter to pass through the smaller diameter opening formed in the buttress 12 by the circular stapler cutting blade without causing permanent alteration or damage to the cut edge of the opening formed by the cutting action of the circular stapler blade. Permanent alteration of the cut edge results from tears, rips, or other permanent deformation. Essentially inelastic behavior occurs when an anvil head 16 of larger outer diameter than the smaller diameter opening formed in a buttress 12 by the circular stapler cutting blade causes permanent alteration or damage to the cut edge of the opening formed by the circular stapler cutting blade. The essentially inelastic buttress 12 by definition would rip, tear, or otherwise retain permanent alteration to the cut edge of the opening formed by the circular stapler cutting blade after passing the larger diameter anvil head 16 through the smaller opening formed by the circular stapler cutting blade. A buttress may be made from either relatively elastic (e.g., silicone) or relatively inelastic materials (e.g., PGA:TMC). If made from relatively inelastic materials, the buttress may be fabricated in such a way as to now possess essentially elastic behavior. For example, inelastic materials may be fabricated into a material possessing a degree of porosity, such as a weave or a web, wherein the porosity provides for adequate flexibility thereby allowing the resulting buttress to demonstrate essentially elastic behavior.

The relief features shown in FIGS. 3A-3H, 3J and 3K as well as others can be used with either essentially elastic or essentially inelastic buttresses 12. These relief features will be required, however, for buttresses 12 that without such relief features would exhibit essentially inelastic behavior.

Figure 5A:
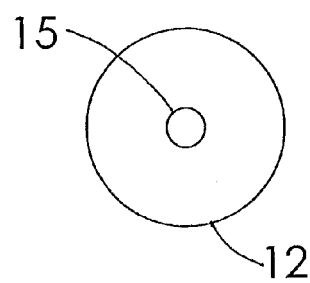
FIGS. 5A-5E show top views of elastic and inelastic buttresses prior to and following central region cut out by the generally circular concentric cutting blade of a circular stapler and following removal of the anvil portion of a circular stapler through the central region hole.
Figure 5B:
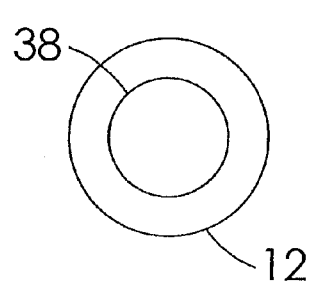
Figure 5C:
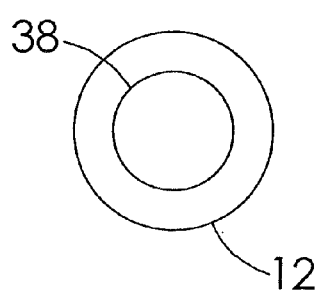

FIG. 5A shows the top view of a buttress 12 which has a central opening 15 sized to closely fit the outside diameter of a central tubular shaft 14 of a circular stapler 10. FIG. 5B shows the top view of a buttress 12 after a hole with a cut edge 38 has been cut through it by the action of a generally circular concentric cutting blade of a circular stapler 10. FIG. 5C shows the top view of a buttress 12 constructed to be elastic after a circular stapler anvil head 16 with a compression surface 18 that has an outer diameter larger than the diameter of the cut edge 38 of the opening formed by the action of a generally circular concentric cutting blade has been passed through it. No substantial permanent alteration or damage is made to the cut edge 38 of the opening formed by the generally circular concentric cutting blade of the circular stapler.

Figure 5D:
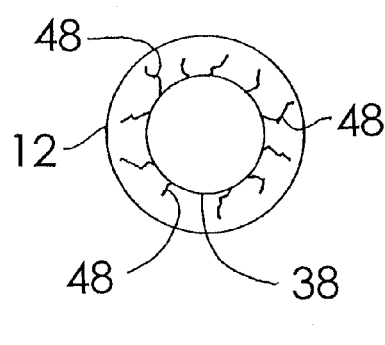
Figure 5E:
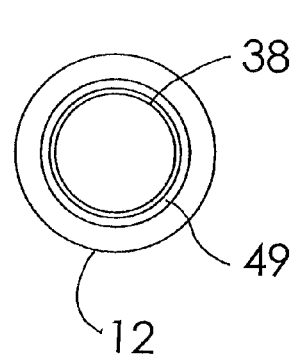
Figure 5G:
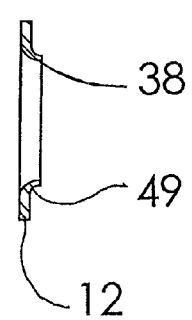
FIG. 5G shows a cross sectional view of an inelastic buttress following removal of the anvil portion of a circular stapler though the hole created by the generally circular concentric cutting blade of a circular stapler.

FIGS. 5D, 5E and 5G show the top and side views of buttresses 12 that are inelastic and without relief features such as shown in FIGS. 3A-3H, 3J and 3K, after pulling through a circular stapler anvil head 16 with a compression surface 18 that has an outer diameter larger than the diameter of the cut edge 38 of an opening formed by the action of a generally circular concentric cutting blade. These buttresses 12 show substantial permanent alteration or damage to the cut edge 38 area of the opening formed by the action of a generally circular concentric cutting blade of a circular stapler 10. FIG. 5D of an inelastic buttress 12 shows tears 48 around the cut edge 38 of the opening caused by pulling through a circular stapler anvil head 16 with a compression surface 18 that has a larger diameter than that of the opening. FIGS. 5E and 5G of an inelastic buttress 12 show deformation 49 around the cut edge 38 of the opening caused by pulling through a circular stapler anvil head 16 with a compression surface 18 that has a larger diameter than that of the opening. Other modes of substantial permanent alteration or damage of the cut edge 38 can be contemplated.

EXAMPLES

Example 1

In order to evaluate the compatibility of buttresses of the present invention with circular staplers, two buttresses of 67% PGA:33% TMC (w/w) having a web density of about 0.5 g/cc were made. These buttresses were made to have a circular shape with an outside diameter of approximately 30 mm, for use with a circular stapler (ILS 29 mm, Ethicon Endosurgery, Somerville N.J.). The buttresses were of uniform thickness of about 0.25 mm, and were provided with a center hole of about 6.3 mm diameter. The central region of each buttress was also provided with a circular silicone stiffener having a diameter of about 19.1 mm and a thickness of about 0.5 mm. Each of these stiffeners was provided with a 6.3 mm diameter hole at its center. One stiffener was adhered to one side of each buttress with the center holes through each component aligned, using MED-1356 silicone adhesive, Nusil technologies, Carpenteria Calif.

A 30 cm section of porcine colon was obtained and cut in half; purse string sutures were made on adjacent ends of the large bowel sections. The anvil, with first buttress in place with the stiffener facing the stapler body, was fed through one section so that the anvil post protruded through the hole in the purse-stringed end. The stapler body, with the shaft extended and with the second buttress in place with the stiffener facing the anvil, was advanced through the adjacent colon tissue until the post protruded through the purse-stringed hole. The anvil post was mated to the body shaft and closed via the actuator knob on the proximal end of the device according to the manufacturer's instructions for use. After firing the stapler and rotating the actuator knob two full turns, the stapler was rotated 90 degrees relative to the anastomosis in both directions and then removed from the colon tissue, pulling the anvil through the anastomosis. Both sides of the anastomosis were observed visually for integrity of the buttresses after removing the anvil (of 28.6 mm outside diameter) through the cut hole (of 20.8 mm diameter). All staples on both sides of the anastomosis were captured and no signs of tearing or disfigurement were observed.

An additional pair of buttresses was fabricated and tested in the same manner. Each buttress of this additional pair was provided with four slits through the thickness of the material, spaced 90 degrees apart and extending radially outward from a point 1.9 mm from the edge of the center hole for a length of 7.6 mm. During testing, this pair was determined to be equally effective as the first pair.

Example 2

Figure 9A:
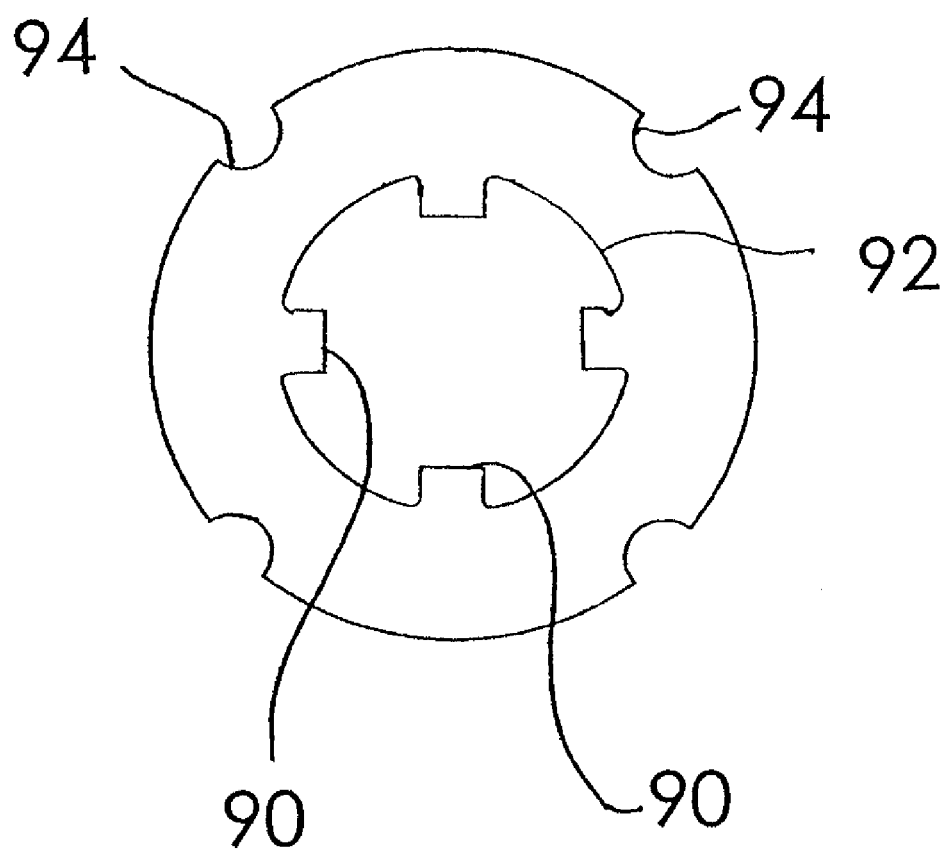
FIG. 9A shows a top view of a first laser cutting pattern that was used to form a preferred embodiment of the device of the present invention.

A preferred embodiment of a buttress with protrusions was made of 67% PGA: 33% TMC (w/w) having a web density of about 0.5 g/cc. using the following method. Two acrylic sheets, each approximately 1.6 mm thick were securely taped with duct tape onto a laser table that had perforations to allow for fume elimination and with a cutting head that was motion controlled by computer. The acrylic sheets were cut with a laser (Laser Machining Incorporated, Model C-42, Somerset, Wis.) into a first pattern as shown in FIG. 9A. A first laser cut was made describing this pattern followed by a second laser cut in the same pattern to insure that both acrylic sheets were cut completely through. The laser cut pieces of acrylic material were then removed from the remainder of the acrylic sheet which was still attached to the laser cutting table by duct tape.

A piece of double coated medical tape with silicone release coating on both sides of the bleached Kraft paper covering both sides of the tape (3M, product number 1509, St. Paul, Minn.) was sized to cover the laser cut pattern shown in FIG. 9A was then placed over the pattern cut into the acrylic sheets which were still securely taped to the laser table. The laser was used to cut through the double coated medical tape and Kraft paper covering both sides of the tape in the pattern shown in FIG. 9A. The piece of double coated medical tape with Kraft paper covering both sides which was cut into the pattern shown in FIG. 9A was then removed from the laser table.

Using a sharp razor blade, the Kraft paper on the top side of the double coated medical tape was carefully peeled away from the each tab 90 from the pattern shown in FIG. 9A to approximately the perimeter of the inner diameter 92 of the pattern shown in FIG. 9A to expose the adhesive tape underneath. The sharp razor blade was then used to score the now exposed adhesive tape at approximately the perimeter of the inner diameter 92 of the pattern, taking care to not cut through the bottom layer of Kraft paper underneath the double coated medical tape. The sharp razor blade was then used to carefully scrape away the double coated medical tape from the bottom layer of Kraft paper from each tab 90 so that the Kraft paper that was underneath the double coated medical tape in the area of each tab 90 was now essentially free of adhesive substance. After scraping off the double coated medical tape from each tab 90, the entire top layer of Kraft paper covering the double coated medical tape was removed, now leaving the pattern shown in FIG. 9A with no double coated medical tape in the areas of each tab 90, but with double coated medical tape on the remainder of the pattern surface.

The double coated medical tape with Kraft paper on the bottom side in the pattern shown in FIG. 9A was then put back onto the laser table and inserted into the cavity left by the pattern that had been cut into the acrylic sheets. The indexing marks 94 which had been cut into the acrylic sheets and the double coated medical tape and Kraft paper were used to align the double coated medical tape and Kraft paper into the pattern cut into the acrylic sheets. The double coated medical tape and Kraft paper pattern was inserted into the cavity left by the pattern that had been cut into the acrylic sheet with the adhesive layer facing up and the now single layer of Kraft paper located between the laser table and the double coated medical tape.

Figure 9B:
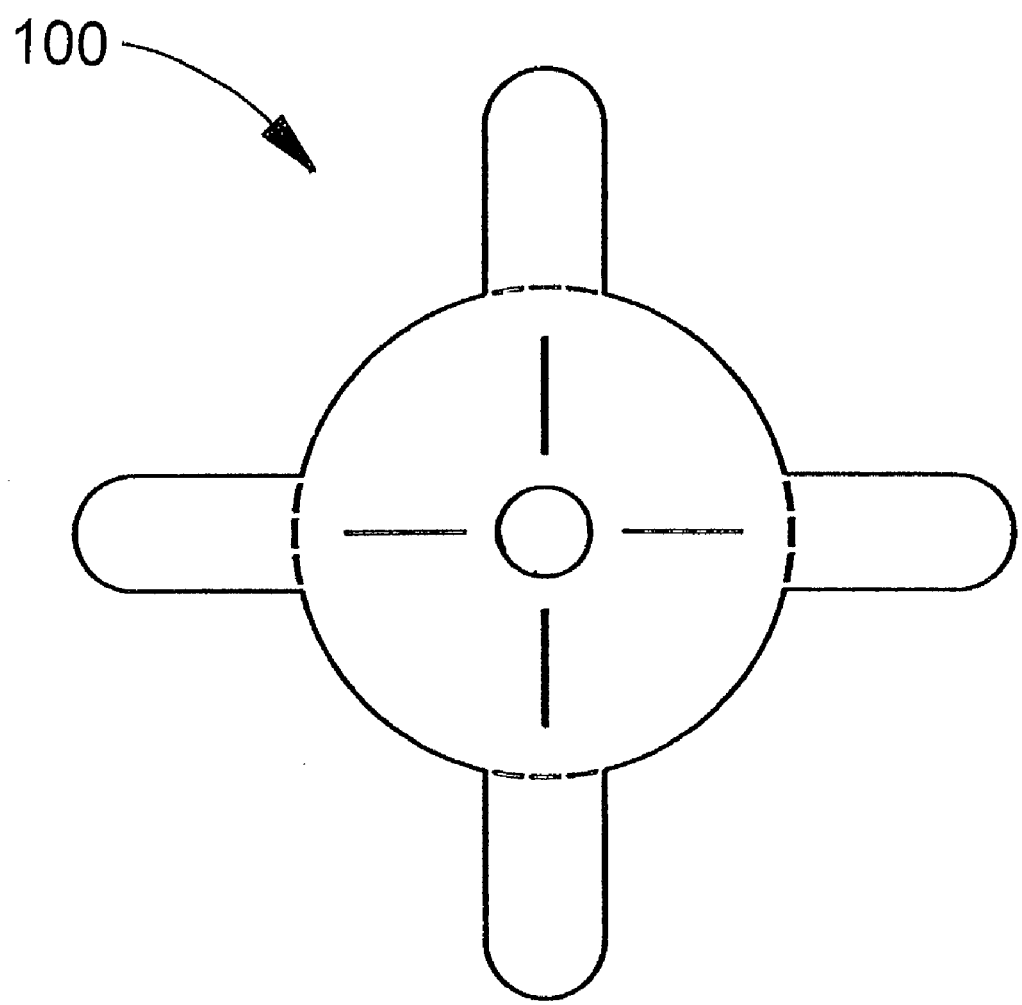
FIG. 9B shows a top view of a second laser cutting pattern that was used to form a preferred embodiment of the device of the present invention.

A layer of 67% PGA: 33% TMC (w/w) material cut large enough to cover the pattern shown in FIG. 9A was then placed onto the exposed adhesive layer of the double coated medical tape on the laser table which allowed the 67% PGA: 33% TMC material to adhere to the double coated medical tape. The laser was then used to cut out a second pattern 100 as shown in FIG. 9B. After removing the excess 67% PGA:33% TMC material and excess double coated medical tape, this process produced the device shown in FIG. 9C which shows a perspective view of a buttress 12 with four removable protrusions 80 extending from the perimeter of the buttress.

Figure 9C:
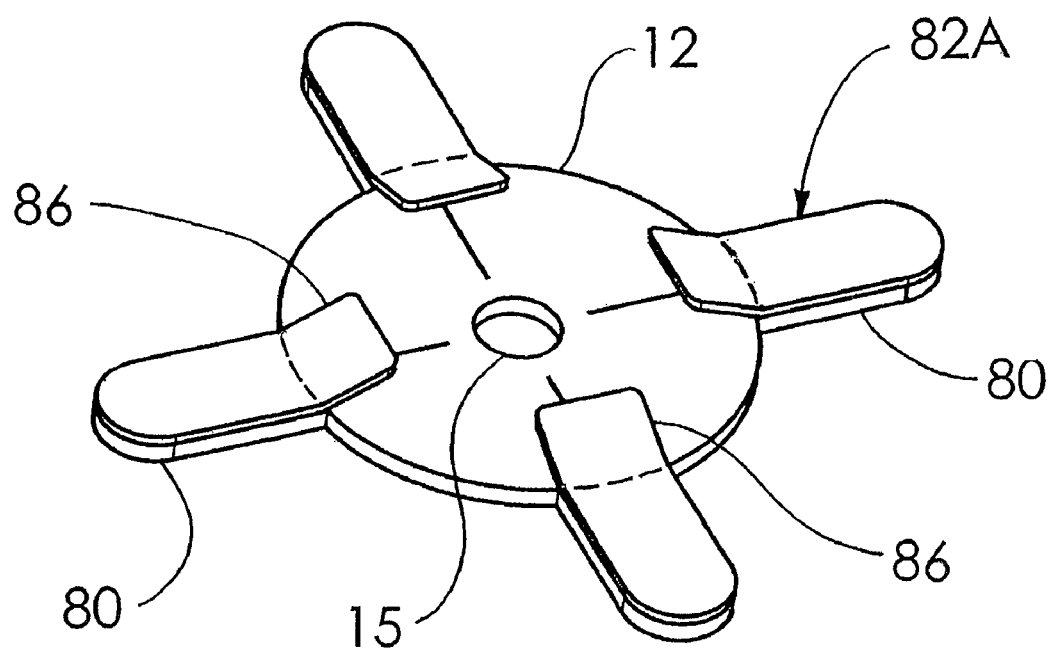
FIG. 9C shows a perspective view of a device of the present invention.

The removable protrusions 80 were covered on one side with the double coated medical tape that coated only the surfaces of the protrusions and not the buttress. The double coated medical tape on one side of the protrusions 80 was covered by perforated removable coverings 82A that protected the adhesive substance on the double coated medical tape from inadvertent contact. Perforated removable coverings 82A as shown in FIG. 9C were only adhered to the protrusions 80 which were coated with the double coated medical tape, but not to the buttress 12, which had no double coated medical tape on it. The tab sections 86 of the perforated removable coverings 82A that overlapped the buttress 12 were not adhered to the buttress 12 because the double coated medical tape on these areas of the removable coverings had been removed as described previously. Removal of the double coated medical tape from these areas of the perforated removable coverings 82A allowed for tab sections 86 that were easily grasped when removal of the coverings 82A was desired.

Buttresses with various inner and outer diameters were made. One buttress 12 made had an inner diameter central opening 15 as depicted in FIG. 9C of approximately 6.3 mm and an outer diameter of approximately 30 mm for use with a circular stapler (ILS 29 mm, Ethicon Endosurgery, Somerville, N.J.). Buttresses of other dimensions were made to fit circular staplers produced by other manufacturers such as the Premium Plus CEEA circular stapler (United States Surgical/Tyco Healthcare, Norwalk, Conn.).

While the principles of the invention have been made clear in the illustrative embodiments set forth herein, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

We claim:

1. An implantable medical device adapted to reinforce tissue stapled together with a circular stapler having a generally circular cutting blade, the device comprising:
    a buttress material adapted for mounting on the circular stapler; and
    a plurality of slits in the buttress material, the slits generally extending in an approximately radial direction,
    wherein, a reinforcing portion of the buttress material is configured to remain stapled to tissue in a patient and an inner portion of the buttress material is configured to be cut away from the reinforcing portion by the cutting blade upon actuation of the circular stapler and cutting blade, resulting in a severed inner edge of the reinforcing portion and a severed outer edge of the inner portion, and
    wherein the slits extend through the severed inner edge of the reinforcing portion.

2. The implantable medical device of claim 1, wherein the slits provide a relief feature to the severed inner edge.

3. The implantable medical device of claim 1, wherein the slits form an expandable inner edge of the reinforcing portion.

4. The implantable medical device of claim 1, wherein the slits facilitate removal of the stapler after actuation.

5. An implantable medical device adapted to reinforce tissue stapled together with a circular stapler having a generally circular cutting blade, the device comprising:
    a buttress material adapted for mounting on the circular stapler;
    a plurality of slits formed in the buttress material, the slits generally extending in an approximately radial direction,
    wherein the slits are located so as to traverse a portion of the buttress material that is configured to be cut by the cutting blade upon actuation of the circular stapler and cutting blade.

6. An implantable medical device adapted to reinforce tissue stapled together with a circular stapler having a generally circular cutting blade, the device comprising:
    a buttress material adapted for mounting on the circular stapler;
    a plurality of slits formed in the buttress material,
    wherein a reinforcing portion of the buttress material is configured to remain stapled to tissue in a patient and an inner portion of the buttress material is configured to be cut away from the reinforcing portion by the cutting blade upon actuation of the circular stapler and cutting blade, resulting in a severed inner edge of the reinforcing portion and a severed outer edge of the inner portion, and
    wherein the slits extend through the severed inner edge of the reinforcing portion.

7. The implantable medical device of claim 6, wherein the slits are configured as a relief feature to the severed inner edge.

8. The implantable medical device of claim 6, wherein the slits are serpentine-shaped.

9. The implantable medical device of claim 6, wherein the slits are triangular.

10. An implantable medical device adapted to reinforce tissue stapled together with a circular stapler having a generally circular cutting blade, the device comprising:
    a buttress material adapted for mounting on the circular stapler and configured to be cut upon actuation of the circular stapler and the cutting blade; and
    a plurality of slits formed in the buttress material, the slits being arranged to traverse a circular portion of the buttress material which is removed by the cutting blade,
    wherein the slits and the edge created by the cutting blade form an adaptive opening that allows the passage of components having a larger diameter than the opening.

11. An implantable medical device adapted to reinforce tissue stapled together with a circular stapler having a generally circular cutting blade, the device comprising:
    a buttress material adapted for mounting on the circular stapler; and
    a plurality of slits formed in the buttress material, the slits being arranged to traverse a cutting line on the buttress material, the cutting line being a generally circular portion of the buttress material that is adapted to be severed by the cutting blade,
    wherein a reinforcing portion of the buttress material remains stapled to tissue in a patient and an inner portion of the buttress material is configured to be cut away from the reinforcing portion by the cutting blade upon actuation of the circular stapler and cutting blade, and the slits extend through the severed edge of the reinforcing portion, thereby creating relief flaps.

12. The implantable medical device of claim 11, wherein each of the slits extend from a point on the buttress material through the severed edge.

13. The implantable medical device of claim 11, wherein the slits allow for the passage of a stapler component having a diameter greater than the diameter of the cutting blade through the center of the buttress material after actuation.

14. A buttress material for reinforcing an anastomosis at a surgical site for use with a circular stapler having a central shaft and a circular cutting blade,
    the buttress material being generally circular in shape, the buttress material having a central region which is configured to be cut away by the cutting blade after firing of the circular stapler, the buttress material further having an outer diameter sized to coincide approximately with the outer diameter of a stapler body compression surface of the circular stapler or with the outer diameter of an anvil compression surface of the circular stapler;

the buttress material having a generally circular opening in the central region configured to allow the central shaft of the circular stapler to pass through the generally circular opening; and the buttress material further having a plurality of slits extending radially towards the outer diameter of the generally circular buttress material, the slits being sized to facilitate removal of the circular stapler from the surgical site after the circular stapler has been fired and the central region has been cut away by the circular cutting blade.

15. The buttress material of claim 14, wherein the slits are configured symmetrically around the circular opening in the central region.

16. The buttress material of claim 15, wherein the slits are equally spaced from each other.

17. The buttress material of claim 14, wherein the diameter of the central region that is cut away by the cutting blade is smaller than the outer diameter of the anvil compression surface.

18. The buttress material of claim 14, further comprising a retaining ring around the central region to aid in retaining the buttress material.

19. The buttress material of claim 14, further comprising a disk to aid in retaining the buttress material.

20. The buttress material of claim 14, wherein the buttress material further comprises a slit extending from the central opening to the outer diameter of the buttress material.

21. The buttress material of claim 14, wherein the buttress material is self-aligning.

22. The buttress material of claim 21, wherein the buttress material comprises a surface that contacts the outer diameter of the anvil compression surface or the outer diameter of the stapler body compression surface.

23. The buttress material of claim 14, further comprising a retaining device to aid in the retention of the buttress material on the circular stapler without requiring the use of an adhesive substance.

24. A buttress material adapted for mounting on a circular stapler having a generally circular blade, the buttress material having an initial inner edge and an initial outer edge; and a plurality of slits in the buttress material, the slits generally extending in an approximately radial direction, said slits extending from the initial inner edge of the buttress material, wherein a reinforcing portion of the buttress material is configured to remain stapled to tissue in a patient and an inner portion of the buttress material is configured to be cut away from the reinforcing portion by the cutting blade upon actuation of the circular stapler and cutting blade, resulting in a severed inner edge of the reinforcing portion and a severed outer edge of the inner portion, and wherein the slits extend through the severed inner edge of the reinforcing portion.

* * * * *